(12) United States Patent
Hulse et al.

(10) Patent No.: US 8,609,909 B2
(45) Date of Patent: Dec. 17, 2013

(54) PROCESS FOR THE PURIFICATION OF HYDROFLUOROOLEFINS

(75) Inventors: Ryan Hulse, Getzville, NY (US); Rajiv Ratna Singh, Getzville, NY (US); Ian Shankland, Randolph, NY (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 709 days.

(21) Appl. No.: 12/696,613

(22) Filed: Jan. 29, 2010

(65) Prior Publication Data

US 2010/0193347 A1  Aug. 5, 2010

Related U.S. Application Data

(60) Provisional application No. 61/148,505, filed on Jan. 30, 2009.

(51) Int. Cl.
*C07C 17/386* (2006.01)
*B01D 3/36* (2006.01)

(52) U.S. Cl.
USPC ............... 570/262; 203/28; 203/59; 570/160

(58) Field of Classification Search
USPC ............................ 203/28, 59; 570/160, 262
See application file for complete search history.

(56) References Cited

U.S. PATENT DOCUMENTS

| | | | | |
|---|---|---|---|---|
| 2,738,371 | A * | 3/1956 | Parmelee | 570/177 |
| 4,369,096 | A * | 1/1983 | Seifert et al. | 203/58 |
| 5,563,306 | A * | 10/1996 | Meinert | 570/177 |
| 7,098,176 | B2 | 8/2006 | Singh et al. | |
| 7,794,618 | B2 * | 9/2010 | Pham et al. | 252/68 |
| 8,252,965 | B2 * | 8/2012 | Merkel et al. | 570/216 |
| 2007/0007488 | A1 * | 1/2007 | Singh et al. | 252/68 |
| 2007/0179324 | A1 | 8/2007 | Van Der Puy et al. | |
| 2008/0292564 | A1 * | 11/2008 | Singh et al. | 424/47 |
| 2010/0187464 | A1 * | 7/2010 | Knapp et al. | 252/2 |
| 2011/0037016 | A1 * | 2/2011 | Singh et al. | 252/67 |

OTHER PUBLICATIONS

Kim, et al., "A Study to Determine the Existence of an Azeotropic R-22 "Drop-In" Substitute," prepared by U.S. Department of Commerce for Electric Power Research Institute, Mar. 1996, pp. 1-45, U.S.

Morrison, et al., "Azeotropy in Refrigerant Mixtures," International Journal of Refrigeration, 1993, pp. 129-138, vol. 16, No. 2. U.S.

* cited by examiner

*Primary Examiner* — Virginia Manoharan
(74) *Attorney, Agent, or Firm* — Bruce O. Bradford

(57) ABSTRACT

Processes for the preparation and purification of hydrofluoroolefins such as tetrafluorinated propenes. A process is provided for separating a first hydrofluoroolefin from a second hydrofluoroolefin by a) providing a mixture including a first hydrofluoroolefin and a second hydrofluoroolefin, which first hydrofluoroolefin is preferentially more reactive with an amine than the second hydrofluoroolefin; b) adding a sufficient amount of an amine to the mixture to form a combination including the second hydrofluoroolefin and a reaction product of the first hydrofluoroolefin and the amine; and then c) separating the reaction product from the combination. This is particularly useful for removing 1,2,3,3,3-pentafluoropropene (HFO-1225ye) impurities from the hydrofluoroolefin 2,3,3,3-tetrafluoropropene (HFO-1234yf). HFO-1234yf is a refrigerant with low global warming potential.

22 Claims, 1 Drawing Sheet

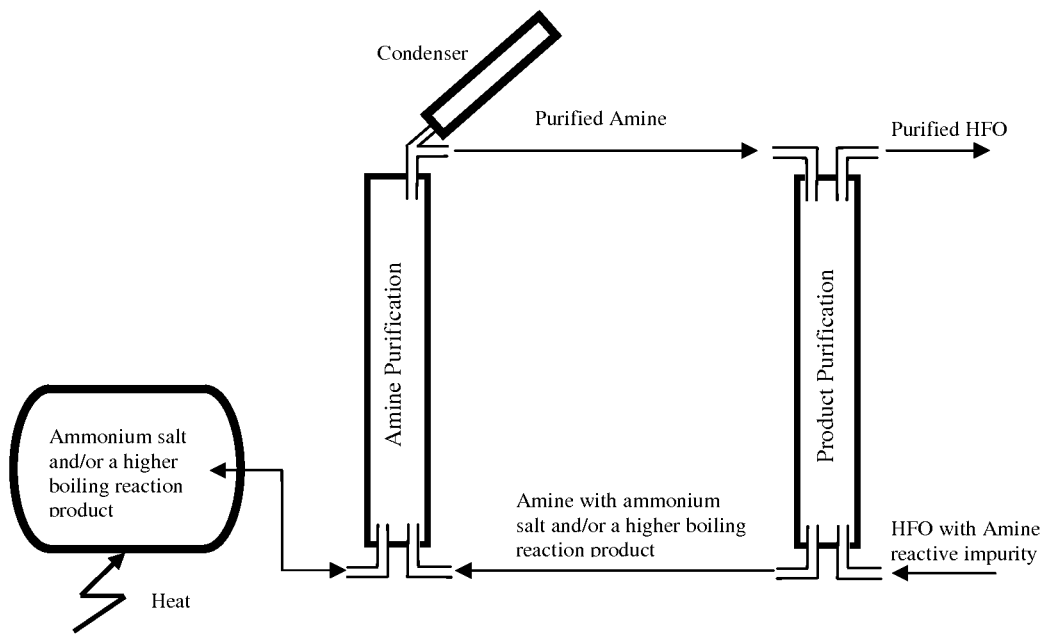

PROCESS FOR THE PURIFICATION OF HYDROFLUOROOLEFINS

CROSS-REFERENCE TO RELATED APPLICATIONS

This application claims the priority benefit of U.S. Provisional Application No. 61/148,505, filed Jan. 30, 2009, which is incorporated herein by reference.

BACKGROUND OF THE INVENTION

1. Field of the Invention

The present invention relates to processes for preparing hydrofluoroolefins such as tetrafluorinated propenes.

2. Description of the Related Art

Fluorocarbon based fluids have found widespread use in many commercial and industrial applications including as refrigerants, aerosol propellants, blowing agents, heat transfer media, gaseous dielectrics and as working fluids in air conditioning, heat pump and refrigeration systems. The vapor compression cycle is one of the most commonly used type methods to accomplish cooling or heating in a refrigeration system. The vapor compression cycle usually involves the phase change of the refrigerant from the liquid to the vapor phase through heat absorption at a relatively low pressure and then from the vapor to the liquid phase through heat removal at a relatively low pressure and temperature, compressing the vapor to a relatively elevated pressure, condensing the vapor to the liquid phase through heat removal at this relatively elevated pressure and temperature, and then reducing the pressure to start the cycle over again. Certain fluorocarbons have been a preferred component in many heat exchange fluids. For, example, fluoroalkanes, such as chlorofluoromethane and chlorofluoroethane derivatives, have gained widespread use as refrigerants in applications including air conditioning and heat pump applications owing to their unique combination of chemical and physical properties. Many of the refrigerants commonly utilized in vapor compression systems are either single components fluids or azeotropic mixtures.

However, suspected environmental problems associated with the use of some of these fluids, including the relatively high global warming potentials associated therewith, it is desirable to use fluids having the lowest possible greenhouse warming potential in addition to zero ozone depletion potential. Thus there is considerable interest in developing environmentally friendlier materials for the applications mentioned above. Concern has increased in recent years about potential damage to the earth's atmosphere and climate, and certain chlorine-based compounds have been identified as particularly problematic in this regard. The use of chlorine-containing compositions (such as chlorofluorocarbons (CFC's), hydrochlorofluorocarbons (HCF's) and the like) as refrigerants in air-conditioning and refrigeration systems has become disfavored because of the ozone-depleting properties associated with many of such compounds. Thus, there is an increased need for new fluorocarbon and hydrofluorocarbon compounds and compositions that offer alternatives for refrigeration and heat pump applications. For example, it has become desirable to retrofit chlorine-containing refrigeration systems by replacing chlorine-containing refrigerants with non-chlorine-containing refrigerant compounds that will not deplete the ozone layer, such as hydrofluorocarbons (HFC's).

Although most HFC's will not deplete the ozone layer, there is concern about the global warming potential (GWP) associated with these molecules. GWP is a measure of the potential contribution to the green house effect of the chemical against a reference, the reference molecule in this case is $CO_2$ which has a GWP=1. Regulation in the European Union has already set limits of a GWP=150 for refrigerants to be used in some applications such as automotive air conditioning.

Hydrofluorocarbons (HFC's), particularly hydrofluoroalkenes such tetrafluoropropenes, have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer. Tetrafluoropropenes, having zero ozone depletion and low global warming potential, have been identified as potentially filling this need. However, the toxicity, boiling point, and other physical properties in this class of chemicals vary greatly from isomer to isomer. One tetrafluoropropene having valuable properties is 2,3,3,3-tetrafluoropropene (HFO-1234yf). Thus, there is a need for new manufacturing processes for the production of tetrafluoropropenes and in particular 2,3,3,3-tetrafluoropropene. 2,3,3,3-Tetrafluoropropene (HFO-1234yf) is a refrigerant that has been designed to meet the EU regulations for automotive air conditioning.

U.S. patent application publication US2007/0179324 discloses a synthesis process involving the dehydrofluorination of 1,1,1,2,3-pentafluoropropane (HFC-245eb) to form HFO-1234yf. Also disclosed is the dehydrofluorination of 1,1,1,2,3,3-hexafluoropropane (HFC-236ea) under similar conditions to form 1,2,3,3,3-pentafluoropropene (HFO-1225ye (Z)). Accordingly, the presence of HFC-236ea impurities in this reaction could produce HFO-1225ye(Z) as an unwanted byproduct. To overcome this issue, US2007/0179324 also discloses that HFO-1225ye(Z) can be reacted with hydrogen to form HFC-245eb, which can be dehydrofluorinated to form HFO-1234yf. However, any HFO-1225ye(Z) which is not fully hydrogenated in the first step will end up as an impurity if the final product stream of HFO-1234yf.

Distillation is a conventional purification method for commercial processes. Distillation takes advantage of the fact that the liquid and vapor of a chemical mixture are at different compositions. However, distillation becomes inefficient and then impossible as the chemical mixture approaches a pinch point and an azeotropic composition, respectively. The closer the composition is to a pinch point the more yield loss there will be in the distillation. This phenomena renders the separation of HFO-1225ye(Z) from a HFO-1234yf product stream using standard distillation techniques very difficult. More particularly, it is very difficult to remove HFO-1225ye (Z) from HFO-1234yf by conventional distillation at very low levels of HFO-1225ye(Z) without large yield losses due to the fact that HFO-1225ye(Z) and HFO-1234yf form an azeotrope (see U.S. Pat. No. 7,098,176).

SUMMARY OF THE INVENTION

This invention provides a method for preparing high purity hydrofluoroolefin by reacting certain undesirable hydrofluoroolefin impurities and/or byproducts with an amine to produce a reaction product having a relatively high boiling point and/or an ammonium salt. The amine reactive impurity can then be removed from the desired composition without significant yield loss. This method is particularly advantageous when separating hydrofluoroolefins having pinch points or azeotropic compositions. For example, this method is especially useful in preferentially reacting a HFO-1225ye(Z) impurity in a HFO-1234yf product stream because it has been found that HFO-1225ye is about 500 times more reactive with amines than HFO-1234yf.

Accordingly, provided is A process for preparing a hydrofluoroolefin comprising (a) providing a first composition having a first hydrofluoroolefin and a second hydrofluoroolefin; (b) contacting said composition with an amine to produce a second composition comprising said second hydrofluoroolefin and a reaction product derived from a reaction between said amine and said first hydrofluorocarbon, wherein said reaction product is an ammonium salt and/or has a boiling point higher than the boiling point of said second hydrofluoroolefin; and (c) separating said reaction product from second composition to produce a purified product, wherein said purified product has a higher concentration of said second hydrofluoroolefin compared to said second composition.

Also provided is a process for purifying a hydrofluoroolefin product stream comprising: (a) providing a first composition comprising a tetrafluoropropene and a pentafluoropropene, wherein said tetrafluoropropene and said pentafluoropropene are present in amounts to form an azeotrope-like mixture; (b) contacting said composition with an amine to produce a non-azeotrope-like product comprising said tetrafluoropropene and a reaction product derived from a reaction between said amine and said pentafluoropropane; and (c) separating said reaction product from said tetrafluoropropene to produce a purified product having a higher concentration of said first hydrofluoroolefin compared to said second composition.

Also provided is a process for separating the components of an azeotrope-like composition comprising: (a) providing a first composition comprising an azeotrope-like mixture of 2,3,3,3-tetrafluoropropene and 1,1,1,2,3-pentafluoropropane; and (b) contacting said mixture with an amine to produce a second composition, wherein said second composition is essentially free of azeotrope-like mixtures.

BRIEF DESCRIPTION OF THE DRAWING

FIG. 1 shows an example of an apparatus useful for the continuous removal of an amine reactive impurity.

DESCRIPTION OF THE INVENTION

In the production of hydrofluoroolefins it is common for the desired hydrofluoroolefin to contain minor amounts of other, undesired hydrofluoroolefins as impurities to be removed. Removal is often difficult due to the close boiling points of the hydrofluoroolefin. Thus the inventive process separates a first hydrofluoroolefin from a second hydrofluoroolefin in a mixture comprising a first hydrofluoroolefin and a second hydrofluoroolefin, in which the first hydrofluoroolefin is preferentially more reactive with an amine than the second hydrofluoroolefin. In a preferred embodiment, the first hydrofluoroolefin comprises 1,2,3,3,3-pentafluoropropene and the second hydrofluoroolefin comprises 2,3,3,3-tetrafluoropropene.

A sufficient amount of an amine is added to the mixture to form a combination comprising the second hydrofluoroolefin and a reaction product of the first hydrofluoroolefin and the amine. Thereafter, the reaction product is separated from the combination. Often the reaction product is a salt formed by reacting the first hydrofluoroolefin and the amine.

Amines useful in the present invention include primary, secondary and tertiary amines. The reactivity of amines with the undesirable hydrofluoroolefin is generally primary>secondary>tertiary. The reactivity of the amine also depends upon the steric hindrance. The more hindered the amine the less reactive it will be. For example, trimethylamine is more reactive than diisopropyl ethyl amine. Accordingly, most preferred amines are not sterically hindered.

Preferably the boiling point of the amine is at least about 20° C. greater than the boiling point of the second hydrofluoroolefin. Preferably the first hydrofluoroolefin is about 100 or more times more reactive with the amine than the second hydrofluoroolefin. More preferably the first hydrofluoroolefin is about 500 or more times more reactive with the amine than the second hydrofluoroolefin. The determination of reaction rates is well known to the skilled artisan. See Chemical Reaction Engineering, Third Edition; by Octave Levenspiel; John Wiley & Sons. 1999; chapter 2 at pages 13-33, which is incorporated herein by reference.

Non-limiting examples of useful amines include at least one of propyl amine, n-butyl amine, ethylenediamine, n-octyl amine, aniline, cyclohexylamine, benzylamine, dimethylamine, diethylamine, dibutylamine, dibenzylamine, morpholine, N-methyl aniline, methylbenzylamine, piperidine, pyrrole, pyrrolidine, pyrrolidinone, piperazine, morpholine, piperidine, pyrrole, pyrrolidine, N-alkylmorpholines, N-alkylalkanolamines, N,N-dialkylcyclohexylamines, and alkylamines where the alkyl groups are methyl, ethyl, propyl, butyl and isomeric forms thereof, triethylamine, diisopropylethylamine, triethylenediamine, tetramethylethylenediamine, bis(2-dimethylaminoethyl)ether, triethylamine, tripropylamine, tributylamine, triamylamine, pyridine, quinoline, dimethylpiperazine, piperazine, N,N-dimethylcycolhexylamine, N-ethylmorpholine, 2-methylpiperazine, N,N-dimethylethanolamine, tetramethylpropanediamine, methyltriethylenediamine, N,N,N',N'',N''-pentamethyldiethylene triamine, and mixtures thereof.

In certain preferred embodiments, the amine is added to the mixture in an amount of up to about a 1:1 mole ratio with the amount of the first hydrofluoroolefin. Once the amine has reacted with the first hydrofluoroolefin, it will create a reaction product which is often an ammonium salt and/or a higher boiling reaction product. These salts and/or a higher boiling reaction products typically can easily be separated from the desired second hydrofluoroolefin in the combination by at least one of evaporation, distillation, absorption or solvent extraction, which are well known techniques to the skilled artisan.

The resulting salts and/or higher boiling reaction products also can easily be separated from the amine. The amine can be purified by simple evaporation and subsequent condensation of the amine which leaves the salt and/or a higher boiling reaction product behind. The regenerated amine can once again be used to react with additional impurity. In a preferred embodiment, the process further comprises the subsequent step of recycling the amine back to the amine reaction step b).

An example of a continuous process which would allow for the amine reactive impurity to be removed is shown in FIG. 1. From FIG. 1 it can be seen that it is preferable to have an amine that boils at least 20° C. higher than the product being purified in order to not have any amine appear in the product stream. The amine purification and product purification columns could be a simple flash tanks or distillation/absorption columns.

The following non-limiting examples serve to illustrate the invention.

EXAMPLE 1

Relative Reactivity of HFO-1234yf and HFO-1225ye Toward an Amine

A glass pressure reactor was charged with a solution of 1.735±0.005 g of N,N,N',N'',N''-pentamethyldiethylene triamine ($Me_2NCH_2CH_2NMeCH_2CH_2NMe_2$) in 50.0 g of a polyol based solvent. The olefin (HFO-1234yf, 3.09 g, 0.027 mol or HFO-1225ye(Z), 3.47 g, 0.026 mol) was then added and the mixture stirred with heating to 130° F. by means of an oil bath. Samples (2-3 mL) were taken periodically. The dissolved olefin in the sample was removed under vacuum and the residue analyzed for inorganic fluoride as an indication of the extent of reaction.

| Olefin | Time (hours) | ppm Fluoride |
|---|---|---|
| HFO-1234yf | 19.0 | 3 |
|  | 67.75 | 11 |
|  | 163 | 31 |
| HFO-1225ye(Z) | 20.5 | 2936 |
|  | 46.0 | 4827 |
|  | 71.75 | 7151 |

When ppm fluoride is plotted against time for each olefin, a straight line is obtained, the slopes of which show that in this test, HFO-1225ye(Z) is over 500 times more reactive than HFO-1234yf.

EXAMPLE 2

Removal of HFO-1225ye(Z) from HFO-1234yf Using Morpholine

A sample of HFO-1234yf which initially contained 935 ppm HFO-1225ye(Z) was bubbled through morpholine at 23° C. and ambient pressure. As the olefin exited the bubbler it was collected in a cylinder cooled by dry ice. The HFO-1225ye(Z) content of the collected material was then analyzed and again bubbled through the morpholine. The olefin was bubbled through the same sample of morpholine 4 consecutive times. A fresh morpholine sample was then placed in the bubbler and the sample was passed through for a 5$^{th}$ time. The results of the HFO-1225ye(Z) analysis indicate that the morpholine is able reduce the HFO-1225ye(Z) concentration by nearly ½. The electrical conductivity of the morpholine was also measured before and after the HFO-1225ye(Z) collection. The increase in the electrical conductivity indicates that a salt has formed from the olefin and morpholine. The salt can be separated from the morpholine by simple evaporation of the morpholine. The purified morpholine can then be recycled to react with additional HFO-1225ye(Z).

TABLE 1

Removal of HFO-1225ye(Z) from HFO-1234yf using Morpholine

| Sample | 1225ye(Z) ppm | Morpholine Conductivity µS/cm |
|---|---|---|
| Initial Material | 935 | 0.00 |
| 1st Pass | 589 |  |
| 2nd Pass | 499 |  |
| 3rd Pass | 470 |  |
| 4th Pass | 472 | 0.03 |
| Fresh Morpholine | | |
| 5th Pass | 295 | |

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for purifying a hydrofluoroolefin product stream comprising:
   a. providing a first composition comprising a tetrafluoropropene and a pentafluoropropene, wherein said tetrafluoropropene and said pentafluoropropene are present in amounts to form an azeotrope-like mixture;
   b. contacting said composition with an amine to produce to non-azeotrope-like product comprising said tetrafluoropropene and a reaction product derived from a reaction between said amine and said pentafluoropropene; and
   c. separating said reaction product from said tetrafluoropropene to produce a purified product having a higher concentration of said tetrafluoropropene compared to said non-azeotrope-like product.

2. The process of claim 1 wherein said a non-azeotrope-like product comprises a majority of said tetrafluoropropene from said first composition.

3. The process of claim 1 wherein said purified product comprises less pentafluoropropene compared to said first composition.

4. The process of claim 1 wherein said first composition is provided as a feed stream to a reactor.

5. The process of claim 1 wherein said non-azeotrope-like product further comprising at least a portion of said amine from step (b) and wherein said process further comprises
   d. separating said amine from said non-azeotrope-like product and recycling said amine so separated to step (b).

6. The process of claim 1 wherein the pentafluoropropene is about 100 or more times more reactive with the amine than the tetrafluroropropene.

7. The process of claim 1 wherein the pentafluoropropene is about 500 or more times more reactive with the amine than the tetrafluoropropene.

8. The process of claim 1 wherein the reaction product is separated from the tetrafluoropropene by at least one of evaporation, distillation., absorption or solvent extraction.

9. The process of claim 1 wherein the pentafluoropropene comprises 1,2,3:3,3-pentafluoropropene.

10. The process of claim 1 wherein the tetrafluoropropene comprises 2,3,3,3-tetrafluoropropene.

11. The process of claim 1 wherein the pentafluoropropene comprises 1,2,3,3,3-pentafluoropropene and wherein the tetrafluoropropene comprises 2,3,3,3-tetrafluoropropene.

12. The process of claim 1 wherein the amine has a boiling point that is at least about 20° C. higher than the boiling point of the tetrafluoropropene.

13. The process of claim 1 wherein the amine is selected from the group consisting of propyl amine, n-butyl amine, ethylenediamine, n-octyl amine, aniline, cyclohexylamine, benzylamine, dimethylamine, diethylamine, dibutylamine, dibenzylamine, morpholine, N-methyl aniline, methylbenzylamine, piperidine, pyrrole, pyrrolidine, pyrrolidinone, piperazine, morpholine, piperidine, pyrrole, pyrrolidine, N-alkylmorpholines, N-alkylalkanolimines, N,N-dialkylcyclohexylamines, alkylamines and mixtures thereof, where the alkyl groups are selected from the group consisting of methyl, ethyl, propyl, butyl and isomeric forms thereof.

14. The process of claim 1 wherein said contacting involves adding said amine to the first composition in an amount of up to about a 1:1 mole ratio relative to the pentafluoropropene.

15. The process of claim 1 wherein the amine is selected from the group consisting of triethylamine, diisoplopylethylamine, triethylenediamine, tetramethylethylenediamine, bis(2-dimethylaminoethyl)ether, triethylamine, tripropvlamine, tributylamine, triamylamine, pyridine, quinoline, dimethylpiperazine, piperazine, N,N -dimethylcycolhexylamine, N-ethylmorpholine, 2-methylpiperazine, N,N-dimethylethanolamine, tetramethylpropanediamine, methyltriethylenediamine, N,N,N',N'',N''-pentamethyldiethylene triamine, and mixtures thereof.

16. A process for separating the components of an azeotrope-like composition comprising:
  a. providing a first composition comprising an azeotrope-like mixture of 2,3,3,3-tetrafluroropropene and 1,1,1,2,3-pentafluoropropene; and
  b. contacting said mixture with an amine to produce a second composition comprising said 2,3,3,3- tetrafluroropropene and a reaction product derived from a reaction between said amine and said 1,1,1,2,3- pentafluoropropene, wherein said second composition is essentially free of azeotrope-like mixtures.

17. The process of claim 16 further comprising, separating said reaction product from said 2,3,3,3-tetrafluoropropene to produce a purified product having a higher concentration of said 2,3,3,3-tetrafluoropropene compared to said non- azeotrope-like product.

18. The process of claim 17 wherein the reaction product is separated from the tetrafluoropropene by at. least one of evaporation, distillation, absorption or solvent extraction.

19. The process of claim 16 wherein the amine has a boiling point that is at least about 20° C. higher than the boiling point of the 2,3,3,3-tetrafluoropropene.

20. The process of claim 16 wherein the amine is selected from the group consisting of propyl amine, n-butyl amine, ethylenediamine, n-octyl amine, aniline, cyclohexylamine, benzylamine, dimethylamine, diethylamine, dibutylamine, dibenzylamine, morpholine, N-methyl aniline, methylbenzylamine, piperidine, pyrrole, pyrrolidine, pyrrolidinone, piperazine, morpholine, piperidine, pyrrole, pyrrolidine, N-alkylmorpholines, N-alkylalkanolamines, N,N-dialkylcyclohexylamines, alkylamines and mixtures thereof, where the alkyl groups are selected from the group consisting of methyl, ethyl, propyl, butyl and isomeric forms thereof.

21. The process of claim 16 wherein said contacting involves adding said amine to the first composition in an amount of up to about a 1: 1mole ratio relative to the 1,1,1,2, 3-pentafluoropropene.

22. The process of claim 16 wherein the amine is selected from the group consisting of triethylamine, diisopropylethylamine, triethylenediamine, tetramethylethylenediamine, bis(2-dimethylaminoethyl)ether, triethylamine, tripropylamine, tributylamine, triamylamine, pyridine, quinoline, dimethylpiperazine, piperazine, N, N-dimethylcycolhexylamine, N-ethyltmorpholine, 2-methylpiperazine, N,N-dimethylethanolamine, tetramethylpropanediamine, methyltriethylenediamine, N,N,N',N'',N''-pentamethyldiethylene triamine, and mixtures thereof.

* * * * *